United States Patent
Barkhahn et al.

(10) Patent No.: US 7,758,549 B2
(45) Date of Patent: Jul. 20, 2010

(54) INJECTION NEEDLE ASSEMBLY COMPRISING AN INJECTION NEEDLE AND A NEEDLE GUIDE

(75) Inventors: Susanne Barkhahn, Bern (CH); Andreas Reinmann, Luterbach (CH)

(73) Assignee: Roche Diagnostics International AG, Steinhausen (CH)

(*) Notice: Subject to any disclaimer, the term of this patent is extended or adjusted under 35 U.S.C. 154(b) by 1014 days.

(21) Appl. No.: 11/456,698

(22) Filed: Jul. 11, 2006

(65) Prior Publication Data
US 2007/0016150 A1    Jan. 18, 2007

Related U.S. Application Data (63) Continuation of application No. PCT/EP2005/000318, filed on Jan. 14, 2005.

(51) Int. Cl.
*A61M 5/32* (2006.01)
(52) U.S. Cl. .................. 604/192; 604/198; 604/103.14
(58) Field of Classification Search .............. 604/890.1, 604/892.1, 48, 93.01, 256, 246, 115, 162–163, 604/164.01, 164.03, 164.1, 244, 132, 198, 604/199, 192, 285–286, 96.01, 98.02, 103.06, 604/103.14, 105–106; 128/DIG. 12
See application file for complete search history.

(56) References Cited

U.S. PATENT DOCUMENTS

| 2,403,074 | A | * | 7/1946 | Goldsmith | .................. 604/195 |
| 4,645,495 | A | | 2/1987 | Vaillancourt | |
| 4,857,060 | A | * | 8/1989 | Rosenberg | .................. 604/192 |
| 5,070,886 | A | * | 12/1991 | Mitchen et al. | ............. 600/584 |
| 5,147,308 | A | * | 9/1992 | Singer | ........................ 604/117 |
| 5,267,974 | A | * | 12/1993 | Lambert | ..................... 604/195 |
| 5,304,148 | A | * | 4/1994 | Lannoye et al. | ............. 604/192 |
| 5,607,401 | A | | 3/1997 | Humphrey | |
| 6,126,637 | A | * | 10/2000 | Kriesel et al. | ............... 604/132 |
| 6,238,371 | B1 | | 5/2001 | Himbert et al. | |
| 2005/0177113 | A1 | * | 8/2005 | Bertheas | ..................... 604/192 |

FOREIGN PATENT DOCUMENTS

| DE | 201 01 059 U1 | 9/2002 |
| FR | 2 839 649 | 11/2003 |
| GB | 1 456 725 | 11/1976 |
| WO | WO 2004/047888 A1 | 6/2004 |

* cited by examiner

*Primary Examiner*—Nicholas D Lucchesi
*Assistant Examiner*—Quynh-Nhu H Vu
(74) *Attorney, Agent, or Firm*—Dinsmore & Shohl LLP (57) ABSTRACT

An injection needle assembly including an injection needle, which can pierce body tissue, and a needle guide, which can be placed on the body tissue and axially stabilizes the injection needle against flexure and cracking.

11 Claims, 4 Drawing Sheets

INJECTION NEEDLE ASSEMBLY COMPRISING AN INJECTION NEEDLE AND A NEEDLE GUIDE

CROSS-REFERENCE TO RELATED APPLICATION(S)

This application is a continuation of International Patent Application PCT/EP2005/000318, filed on Jan. 14, 2005, which claims priority to German Application No. 10 2004 002 476.6, filed on Jan. 16, 2004, the entire contents of both of which are incorporated herein by reference.

BACKGROUND

The present invention relates to devices for delivering, injecting, administering or dispensing a substance, and to methods of making and using such devices. More particularly, it relates to an injection needle assembly comprising an injection needle that can be inserted into a body tissue to introduce a product or substance into the body tissue in the context of a therapeutic method, a diagnostic method or, more generally, a medical or cosmetic application. In some embodiments, the product or substance may be introduced subcutaneously, as can happen, for example, in the administration of insulin. In some embodiments, the injection needle assembly may comprise an infusion set and, in some embodiments, it may comprise a perfusion set for perfusion of body fluid, for example for diagnostic purposes.

To introduce liquids, e.g., medically active liquids in therapeutic procedures, flushing liquids in diagnostic procedures, etc., it is customary to use injection needles made of steel. The steel needles are used to penetrate the skin and to penetrate into the underlying, softer body tissue, and also to introduce the product specific to the application. In many applications, particularly in the case of infusion, the injection needle remains in the body tissue at the injection site for a considerable period of time, often for several days. In treatment of diabetes, for example, portable infusion appliances are permanently worn on or under the clothing, to supply the patient with insulin as and when required or almost continuously. The product is delivered or administered via a needle which is inserted into the body tissue and normally remains there for several days. Generally speaking, but in particular when using a portable appliance, the needle inserted into the body tissue has to be flexible, i.e. in this case bendable, to ensure that the needle causes the least possible inconvenience. Steel needles, including thin steel needles of, for example, 28 or 29 G or thinner, have the flexural rigidity and buckling resistance needed for penetration into body tissue, but, in the implanted state, the properties that are advantageous for penetration become problematic, because the patient feels the needle lying in the body tissue each time he or she moves.

To satisfy these contradictory objectives, namely of sufficient flexural rigidity and buckling resistance for penetration and of the lowest possible flexural rigidity with preservation of the cross section of flow through the needle, injection needle assemblies are known, for example from DE 198 21 723 A1, which comprise a steel needle and a flexible needle tightly surrounding the steel needle. The steel needle serves only for introducing the flexible needle into the body tissue. In doing so, it stabilizes the flexible needle. After the introduction, the steel needle is withdrawn from the body tissue, and only the flexible needle remains in the body tissue, the product then being administered through said flexible needle. The combination of injection needle and administration needles requires additional work because it is necessary to seal the injection needle assembly after the injection needle is withdrawn.

SUMMARY

An object of the present invention to make available an injection needle assembly with an injection needle which, as the expression "injection needle" suggests, is itself inserted into the body tissue, into and through the human skin, and causes the least possible discomfort in the inserted state.

In one embodiment, the present invention comprises an injection needle assembly comprising an injection needle and a needle guide for axially stabilizing the injection needle against flexure and cracking.

One embodiment of the present invention comprises, in an injection needle or cannula assembly with an injection needle that can be inserted into body tissue, a needle guide arranged outside the body tissue. The needle guide can be positioned on the body tissue, i.e. placed thereon and fixed, and stabilizes the injection needle, axially movably relative to the needle guide, against bending and buckling. This means that the needle guide laterally supports the injection needle, during insertion, in a penetrating portion that subsequently penetrates into the body tissue. In principle, a single support point between a needle tip and the proximal end of the penetrating portion of the needle is sufficient for this purpose. However, in some embodiments, the needle guide forms several support points between the needle tip and the proximal end of the penetrating portion. In some preferred embodiments, the needle guide also continuously supports the injection needle along the entire length or most of the length of the penetrating portion. The axial guide for the injection needle, as provided by the needle guide, should be free of play or at least have minimal play. If the needle guide forms a single support point, the support point should be situated closer to the needle tip than to the proximal end of the penetrating portion, in some embodiments as close as possible to the needle tip. The needle guide expediently forms an axial slide guide for the injection needle.

Since, during the piercing of the tissue surface, e.g., the surface of the human skin, and also during the further penetration into the body tissue, into the deeper-lying layers of skin and/or into the subcutaneous tissue, the injection needle is stabilized outside the body tissue by means of the free bending length of the injection needle being reduced compared to conventional injection needles, the injection needle according to the invention can be more flexible, namely more bendable, that conventional injection needles. It must, of course, be ensured that a cross section of flow required for introducing the product is maintained.

The invention advantageously allows the injection needle to be made from plastic. However, the use of a steel needle is not excluded. Such a steel needle can still be thinner than conventional steel needles and/or have a smaller wall thickness. As a result, the invention permits the use of non-steel needles, namely needles made from a material having a lower modulus of elasticity than steel, a reduction in the external diameter of the needle or a reduction in the wall thickness of the needle, or the use of a needle that combines several of the stated advantages. With at least the same or greater flexibility as a result of reduction of the modulus of elasticity, the injection needle can have an advantageously large cross section of flow in relation to the flow resistance in some applications. Moreover, the advantage of flexibility does not have to entail the disadvantage of using a supporting injection needle that has to be removed again after introduction into the body tissue. Instead, the injection needle of the injection needle assembly according to the present invention is able to form a flow channel for the administered product before, during and after introduction, so that additional sealing measures are not required, and air can be very easily and completely removed from the injection needle assembly even before introduction.

In some preferred embodiments, the needle guide surrounds the injection needle at least as far as the tip thereof and, in some preferred embodiments, may extend beyond the tip. The needle guide thus also performs a protective function, since it protects the injection needle from damage and protects the user from needlestick injuries before the needle is inserted into the skin.

In some preferred embodiments, the needle guide can be axially deformed into a state of minimal axial thickness. The fact that the needle guide can be deformed into the state of minimal axial thickness means that the needle guide, before deformation, has an axial thickness that corresponds to the sum of minimal axial thickness plus the length of the penetrating portion inserted into the body tissue.

For allowing it to remain at the injection site, it is advantageous if the needle guide deforms permanently during insertion into the skin. It can be advantageous in this respect if it is able to axially deform elastically in a first phase of the deformation, at any rate before the state of minimal axial thickness is reached. In the case of this kind of initial elastic deformability, the range of the elasticity may be left before the pressure force needed for piercing the tissue surface is reached.

In some preferred embodiments, the needle guide is not just positioned at the injection site, but at the same time also fixed there, e.g., by an adhesive which is present on its underside and which can be formed in the manner known from plasters. In these developments, the needle guide thus at the same time ensures adhesion of the injection needle assembly to the tissue surface.

In some embodiments, the needle guide is designed such that, in the axially deformed state, namely in the compressed state, it can serve as a plaster by which the injection needle can be fixed or is fixed at the injection site in the inserted state. For this purpose, the needle guide has at least one adhesive surface directed toward the body tissue and used for fixing it to the body tissue. The adhesive surface can be formed on the underside of the needle guide with which, in some preferred embodiments, the needle guide is already adhesively fixed on the body tissue before insertion into the skin. For some embodiments, it is advantageous if the needle guide has further adhesive surfaces on its underside in areas which are in contact with the body tissue only in the compressed state. These are surfaces which are brought into contact with the surface of the body tissue as a result of the deformation and which are arranged proximally from that surface already in contact, e.g., in adhesive contact, with the body tissue as a result of the placement of the injection needle assembly. Such outer adhesive surfaces may alone suffice to hold the needle guide in the compressed state.

In some preferred embodiments, the needle guide has inner surfaces which are pressed against one another and adhere to one another in an axially compressed state of the needle guide. Such inner adhesive surfaces, or at least one inner adhesive surface, may alone suffice to form a flat plaster in conjunction with the outer adhesive surface that is already adhering after placement of the assembly or in conjunction with an outer adhesive surface brought into contact with the body tissue by means of the deformation. However, the needle guide may also be provided with at least one outer adhesive surface and at least one inner adhesive surface in combination.

In some preferred embodiments, a top face of the needle guide, directed away from the body tissue during insertion, is provided with a force distributor via which a force required for inserting the injection needle into the skin is transmitted to the needle guide. The force distributor forms the support of the injection needle. The injection needle can be secured on the force distributor or can be an integral part of the force distributor. It protrudes freely from the force distributor and into the needle guide, the needle portion protruding freely from the force distributor being supported at least at one position by the needle guide. The force distributor is secured on the top face of the needle guide, but could in principle also lie free on the surface. The force distributor can also be an integral part of the needle guide.

In some preferred embodiments, the needle guide comprises a hollow chamber structure which is axially compressible and surrounds and supports the injection needle.

The hollow chamber structure can be a cell structure with a multiplicity of cells configured and arranged, either regularly or irregularly, in such a way that the cell structure or cell composite has less compression strength axially than it does transversely to the injection needle. The cell structure can, for example, be a honeycomb structure, honeycomb structure being understood as meaning any cross-sectional shape of generally hollow cells, for example including a rectangular or quadratic cross-sectional shape. In some embodiments, no cell walls, or the least possible number of cells walls, should extend in the axial direction. The honeycomb walls should point transversely with respect to the injection needle. Apart from such honeycomb structures, the cell body can also quite simply be a porous body with randomly distributed porosity. Thus, for example, the cell body can have the porous structure of a sponge, i.e. a closed porosity. A configuration with an open porosity is also conceivable, however.

In one preferred alternative embodiment, the hollow chamber structure is formed by a gas-filled balloon. It is also possible for a plurality of gas-filled balloons to jointly form the hollow chamber structure. The wall of the balloon or the walls of the plurality of balloons is or are nonelastic, but still flexible. A certain elasticity of the needle guide is obtained, however, through the gas, e.g., air, contained in the inside of the balloon of or the plurality of balloons. The pressure force that has to be exerted to insert the needle into the skin causes the balloon or balloons to burst. To achieve this, the needle guide can have a puncture device for piercing the balloon or the plurality of balloons. However, in some embodiments, the bursting effect is achieved by a suitable choice of the material properties of the balloon wall, by means of the wall having a tear resistance which ensures safe handling before injection and ensures a bursting effect when a pressure forced required for the injection is reached. When the hollow chamber structure is designed as a gas-filled balloon, in some preferred embodiments, the balloon or each of the plurality of balloons accommodates at least one planar support structure which extends transversely with respect to the injection needle and which supports the balloon or the respective balloon. The support structure should be so flat that it contributes only insignificantly to the axial thickness of the flat plaster advantageously obtained from the balloon or from the plurality of balloons after insertion of the injection needle into the skin.

In some embodiments, the injection needle can have one or more outer channels for delivery of the fluid, i.e. guide channels which are open on the outer circumference of the injection needle. However, in some embodiments, the injection needle is configured as a cannula, i.e. as a hollow needle with an inner lumen for the product to pass through. As used herein, the words "cannula" and "needle" are intended to mean structures suitable for delivering, dispensing, administering, conveying, injecting or sampling substances, including such structures with one or more interior or exterior substance conveying channels, and including such structures exhibiting a degree of rigidity and/or flexibility, e.g. needles, cannulas, catheters, tubes, conduits, etc.

DETAILED DESCRIPTION

Figure 1:
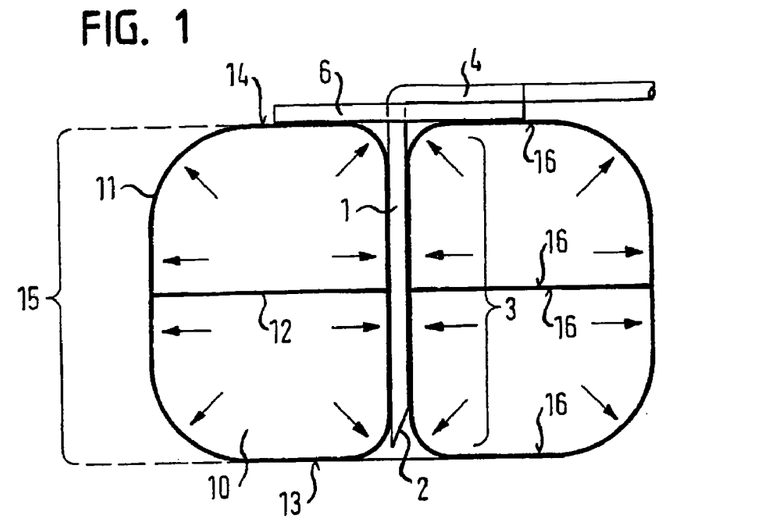
FIG. 1 shows a first illustrative embodiment of a cannula assembly with an injection cannula and a cannula guide.

FIG. 1 shows, in a first illustrative embodiment, a cannula assembly consisting of an injection cannula 1, a cannula guide 10 for the injection cannula 1, and a pressure force distributor 6. The cannula assembly serves for subcutaneous administration of a liquid product, e.g. a medicament, for example insulin. The injection cannula 1 has a penetrating portion 3 with a length dimensioned for the subcutaneous administration and with a free cannula tip 2 at its distal end. The proximal end of the penetrating portion 3 is adjoined by a securing portion 4 which is at an angle, in the illustrative embodiment at a right angle, to the penetrating portion 3. The penetrating portion 3 and the securing portion 4 are made in one piece from a plastic material. The securing portion 4 is connected to a catheter for delivery of the product, in the present illustrative embodiment a liquid medicament. The securing portion 4 lies on a top face of the pressure force distributor 6 and, at the area of the angle, is guided through a central passage of the pressure force distributor 6 so that the penetrating portion 3 protrudes freely from the underside of the pressure force distributor 6 and at right angles to said underside. If the injection cannula is inclined relative to a tissue surface for the purpose of oblique insertion through the skin, the angle would be obtuse, for example 120°. The pressure force distributor 6 has a planar configuration, in the form of a round plate in the illustrative embodiment.

The injection cannula 1 and the pressure force distributor 6 are separately produced parts. The injection cannula 1 is held with frictional engagement in the central passage of the pressure force distributor 6 and is secured lying flat on the top face of the pressure force distributor 6. In a modified design, the injection cannula 1 and the pressure force distributor 6 can also be formed in one piece, or the injection cannula 1 can be embedded with its securing portion 4 in the pressure force distributor 6 and cohesively connected to the pressure force distributor 6.

The cannula guide 10 is an air-filled balloon with a flexible balloon wall 11, so that a cannula guide is obtained which has a flexible axial portion 15 between an underside 13 and a top face 14. The balloon 10 is annular and encloses the penetrating portion 3 of the injection cannula 1. The cannula tip 2 is set back a short distance behind an underside 13 of the balloon 10. The pressure force distributor 6 is secured lying on the top face 14 of the balloon 10. The balloon 10 bears with its internal pressure uniformly over the entire penetrating portion 3. The internal pressure of the balloon 10 is at least as great as the atmospheric pressure, and an overpressure prevails inside the balloon wall 11.

Arranged in the balloon 10 there is a support structure 12, approximately at the axial center of the penetrating portion 3. The support structure 12, as the name is intended to suggest, is planar and flat in the axial direction, i.e. in the longitudinal direction of the injection cannula 1. In the illustrative embodiment, the support structure is a thin support plate, e.g., a support membrane, which can be deformed into a flat shell. The support structure 12 extends, transversely with respect to the injection cannula 1, across the entire radial width of the balloon 10, from its annular outside wall to its annular inside wall, and thus forms, in addition to the annular inside wall of the balloon 10 running along the length of the penetrating portion 3, a local support for the injection cannula 1.

The underside 13 of the balloon 10 is provided, for example coated, with an adhesive, so that an outer adhesive surface is obtained which ensures an adhesive connection of the cannula assembly 10 to the surface of the body tissue, generally the surface of the skin. The coating may be in the form of a layer or a portion of the wall of the balloon may be formed to have adhesive properties. The balloon wall 11 is likewise provided with an adhesive across its entire inner surface. Similarly, the support structure 12 is also provided with an adhesive on its underside directed toward the underside 13 and on its top face directed toward the top face 14. In this way, inner adhesive surfaces 16 are obtained which adhere to one another in a collapsed state of the balloon 10. It would in principle also suffice to provide an adhesive only on the underside and top face of the planar support structure 12 and/or only on the inner surfaces of the balloon wall 11 on the underside 13 and top face 14 of the balloon 10.

Figure 2:
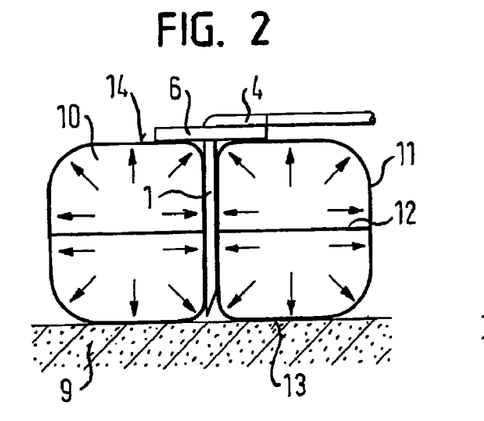
FIG. 2 shows the cannula assembly of the first illustrative embodiment positioned on body tissue.
Figure 3:
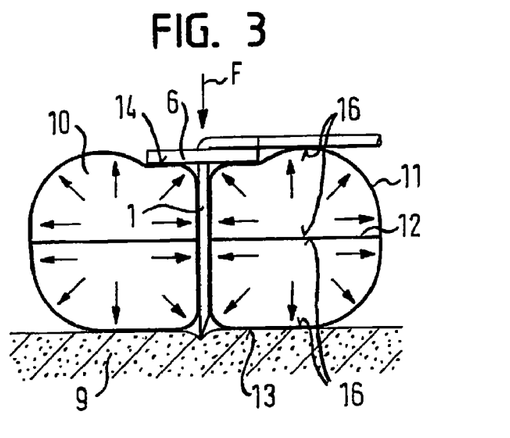
FIG. 3 shows the cannula assembly of the first illustrative embodiment positioned on the body tissue and acted on by an axial pressure force.
Figure 4:
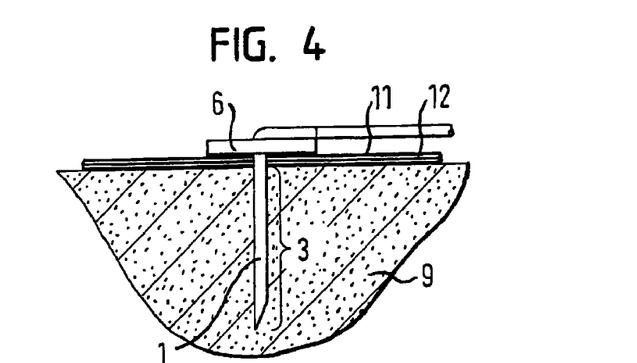
FIG. 4 shows the cannula assembly of the first illustrative embodiment positioned on the body tissue after insertion of the injection cannula into the skin.

FIGS. 2, 3 and 4 show the cannula assembly of the first illustrative embodiment in use.

In FIG. 2, the cannula assembly is placed on the surface of the body tissue 9 and fixed adhesively by means of its underside 13 formed as an outer adhesive surface. No external force is applied to the cannula assembly, or at most a light pressure force which is directed axially in the direction of the surface of the body tissue 9 and which is sufficient to establish the adhesive connection. The cannula tip 2 is located a short distance above the surface of the body tissue 9, i.e. there is still no contact with the body tissue 9.

FIG. 3 shows the cannula assembly of the first illustrative embodiment in the initial phase of insertion of the injection cannula 1 into the skin. By means of a pressure force F exerted on the pressure force distributor 6 in axial continuation of the penetrating portion 3 and directed axially in the direction of the body tissue 9, the pressure force distributor 6 presses against the balloon 10 via the top face 14 of said balloon 10, and the latter accordingly deforms under the pressure force F. Because of the pressure force F, the injection cannula 1 moves axially in the direction toward the surface of the body tissue 9, comes into contact with the surface and initially just presses against the surface, until the surface has reached a critical tension at which the cannula tip 2 pierces the surface and penetrates into the body tissue 9. FIG. 3 shows the cannula assembly directly before it pierces the surface of the body tissue 9.

During the movement toward the surface of the body tissue 9, during the piercing of the surface and during the penetration into the body tissue 9, the penetrating portion 3 of the injection cannula 1 slides along the inside wall of the balloon 10 surrounding it. The support structure 12 stabilizes and guides the injection cannula 1 in the first instance. The balloon 10, in which the support structure 12 is accommodated, additionally supports and guides the penetrating portion 3 of the injection cannula 1 throughout the entire injection procedure. The support structure 12 and the balloon 10 thus stabilize the penetrating portion 3 against bending or even buckling. The cannula portion protruding freely from the underside of the pressure force distributor 6, the penetrating portion 3, can therefore have less flexural rigidity, namely a lower modulus of elasticity and/or a lower geometrical moment of inertia, than conventional injection cannulas which are not laterally supported during the piercing of the tissue surface and their onward penetration into the tissue. The injection cannula 1 is accordingly less "bulky" when it is sitting in the body tissue 9 during the administration of product.

The balloon 10 is constructed such that it bursts when its internal pressure exceeds a predetermined limit value. This limit value is provided for through a suitable dimensioning of the balloon wall 11, i.e. through the use of a suitable wall material and through the wall thickness. The balloon wall 11 is configured such that, when the pressure limit value is exceeded, it tears and the balloon 10 suddenly collapses. The design of the balloon 10 is advantageously such that the balloon 10 bursts after the cannula tip 2 is already pressing against the body tissue 9 but when the cannula tip 2 has not yet penetrated the body tissue 9. The penetration, i.e. piercing of the tissue surface, takes place directly together with the collapse of the balloon 10.

The balloon 10, and the cannula guide according to the present invention in general, is also advantageously configured in such a way that, by means of the manual pressure on the top face 14, i.e. the application of the pressure force F, the surface of the body tissue 9 is tensioned at the injection site and, in this way, the pressure force required for penetration of the surface is reduced.

FIG. 4 shows the cannula assembly in the implanted state. The injection cannula 1 protrudes with its penetrating portion 3 into the body tissue 9. The balloon 10 has completely or substantially completely collapsed and forms a flat plaster adhering to the surface of the body tissue 9, since the outer adhesive surface on the underside 13 of the previous balloon 10 adheres to the body tissue 9 and the inner surfaces 16 adhere to one another. In this state, the product is administered through the injection cannula 1 over the course of several days.

Figure 5:
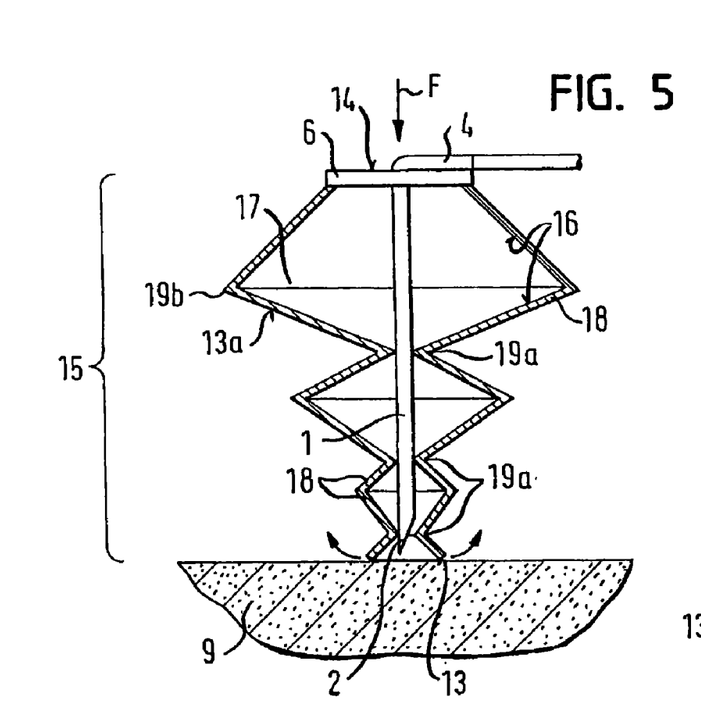
FIG. 5 shows a cannula assembly of another illustrative embodiment positioned on body tissue.

FIG. 5 shows a second illustrative embodiment of a cannula assembly consisting of an injection cannula 1, a pressure force distributor 6 and a cannula guide 17. The injection cannula 1 and the pressure force distributor 6 are designed as in the first illustrative embodiment. The cannula guide 17 also forms a flexible axial portion 15 which, as in the first illustrative embodiment, extends from the underside 13 to the top face 14 of the cannula guide 17. The cannula guide 17 of the second illustrative embodiment is designed as a bellows with pairs of support webs 18 pointing at an angle to one another and to the penetrating portion 3, and folding joints 19a and 19b which are in each case formed between two adjacent support webs 18. The inner folding joints 19a are not only joints, but at the same time also form a supporting and guiding position for the penetrating portion 3.

The support webs 18 are of different lengths, with the length increasing from the underside 13 to the top face 14. Two support webs 18 of identical length are in each case connected to one another in a foldable manner at the outer folding joints 19b. When the assembly is placed in position on the surface of the body tissue 9, the most distal support web 18 points obliquely and radially outward from the most distal inner folding joint 19a, such that an open funnel is obtained on the underside 13. Therefore, as in the first illustrative embodiment, when a pressure force F is exerted, the tissue surface is tensioned at the injection site and, this way, penetration of the tissue surface is made easier.

The bellows structure forming the cannula guide 17 elastically yields in the axial direction when an axial pressure force F is exerted, up to the point where a limit value is reached for the axial pressure force F, but abruptly collapses when the limit value is exceeded. The cannula guide 17 is designed like the cannula guide 10 of the first illustrative embodiment in terms of its deformation properties, as far as the initial elastic resiliency and abrupt collapse are concerned.

Figure 6:
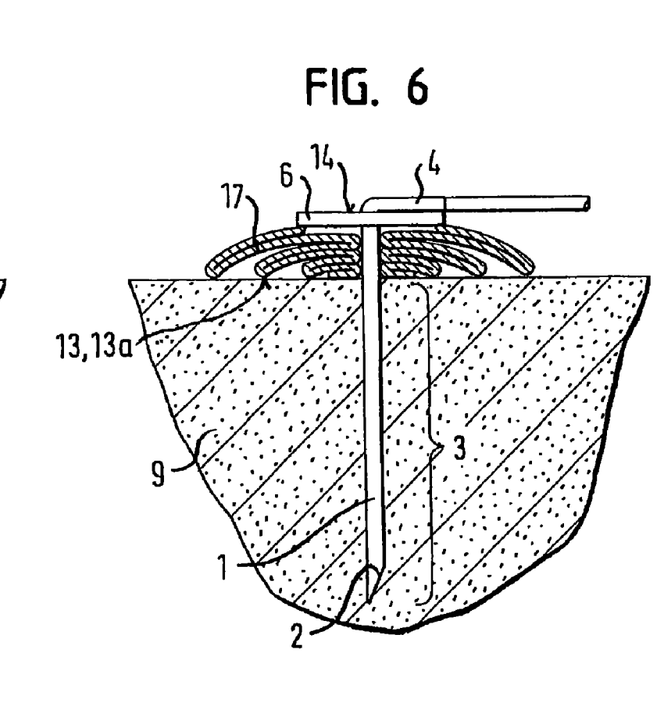
FIG. 6 shows the cannula assembly of the second illustrative embodiment after insertion of the injection cannula into the skin.

FIG. 6 shows the cannula assembly of the second illustrative embodiment in the implanted state of the injection cannula 1, in which the latter's penetrating portion 3 has penetrated into the body tissue 9. In this state, the cannula guide 17 of the second illustrative embodiment likewise forms a flat plaster, because the support webs 18 are folded in pairs on top of one another. To stabilize the cannula guide 17 in the folded state, the support webs 18 are also provided with inner adhesive surfaces 16. Moreover, those support webs 18 with undersides pointing toward the body tissue 9 are provided with outer adhesive surfaces 13a on these undersides, such that the support webs 18 on the one hand adhere to one another via their outer surfaces and, because the support web lengths increase from distal to proximal, they also adhere directly on the surface of the body tissue.

Figure 7:
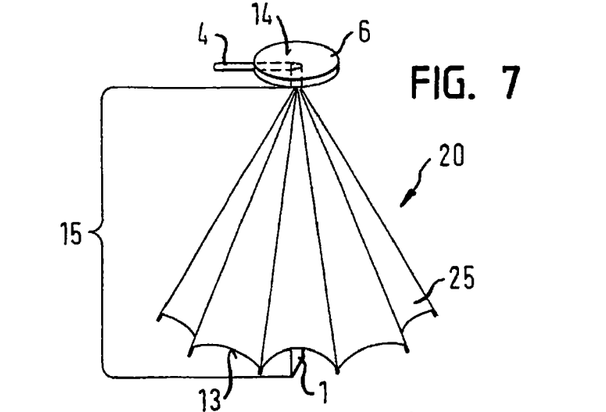
FIG. 7 shows a cannula assembly in another illustrative embodiment.

FIG. 7 shows a cannula assembly of a third illustrative embodiment. The cannula assembly differs from the cannula assemblies of the other illustrative embodiments in terms of its cannula guide 20, which in the third illustrative embodiment is designed as an umbrella structure, i.e., as a structure which can be opened, expanded or spread open in the manner of an umbrella and can be shorted in the length direction of the injection cannula 1.

Figure 8:
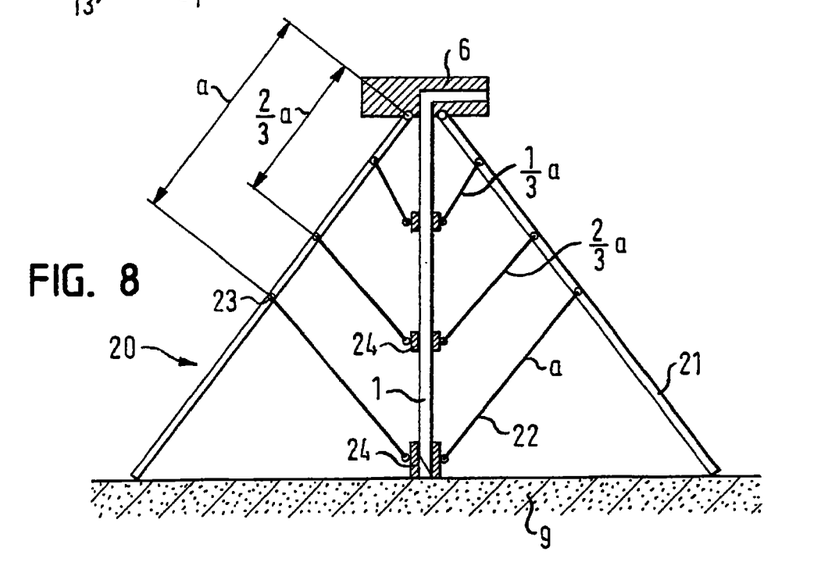
FIG. 8 shows the cannula assembly of the embodiment of FIG. 7 in a longitudinal section.

FIG. 8 shows the cannula assembly of the third illustrative embodiment in a state in which it is placed on the body tissue 9 before insertion of the injection cannula 1 into the skin. As can be seen from FIG. 8, the cannula guide 20 comprises several spreadable struts 21 which are each attached in an articulated manner to an underside of the force distributor 6 directed toward the body tissue 9. The articulated attachment is such that the inherently axially stiff spreadable struts 21 can be pivoted toward the underside of the force distributor 6 at their respective articulation. In relation to the injection cannula 1, the spreadable struts 21 point radially outward from their articulations. They are arranged in uniform distribution around the injection cannula 1. The spreadable struts 21 are each supported on the injection cannula 1 via several support struts 22. The support struts 22 are each attached in an articulated manner to the spreadable struts 21 and form an axial slide guide for the injection cannula 1, which axial guide laterally supports the injection cannula 1 and axially guides it in a linear movement. The articulated attachments of the support struts 22 to the spreadable struts 21 are designated by 23, and the slide guides at the respective other end of the support struts 22 are designated by 24. Along the spreadable struts 21, the articulated attachments 23 are each at a distance from the articulated attachments of the spreadable struts 21 on the force distributor 6 which corresponds to the length of the respective support strut 22. Thus, for example, the support struts 22 which have the greatest distance a from the articulated attachments of the spreadable struts 21 on the force distributor 6 each have a length a corresponding to the distance. The support struts 22 arranged closer to the force distributor 6 each have lengths corresponding to their distances measured along the spreadable struts 21. With uniform distribution, as shown in the illustrative embodiment, lengths 2/3$a$ and 1/3$a$ are obtained for the further support struts 22.

Figure 9:
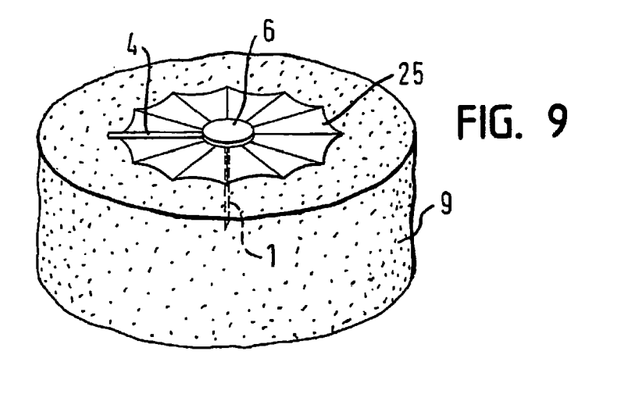
FIG. 9 shows the cannula assembly of the embodiment of FIG. 7 after insertion of the injection cannula into the skin.

FIG. 9 shows the cannula assembly of the third illustrative embodiment with the injection cannula 1 inserted into the body tissue 9. The spreadable struts 21 are pivoted, about their articulated attachments on the force distributor 6, toward the force distributor 6 and are thus spread open. The support struts 22 are pivoted about their articulated attachments 23 toward their respective spreadable strut 21 and come to lie one on the other, so that overall a flat structure is obtained in the spread or compressed state, which flat structure at the same time also serves as a plaster for attachment to the tissue surface.

As is indicated in FIG. 7 and can be seen from FIG. 9, the cannula assembly of the third illustrative embodiment comprises a plaster 25 which, in accordance with the spreading mechanism, can be designated as an umbrella-type plaster. The plaster is similar to the cover of an umbrella. It is secured on or carried by the spreadable struts 21. In the non-inserted state, i.e. before being spread open, it hangs loosely like the cover of an umbrella between the spreadable struts 21, whereas in the inserted state it is stretched out and adheres with its underside on the tissue surface.

Figure 10:
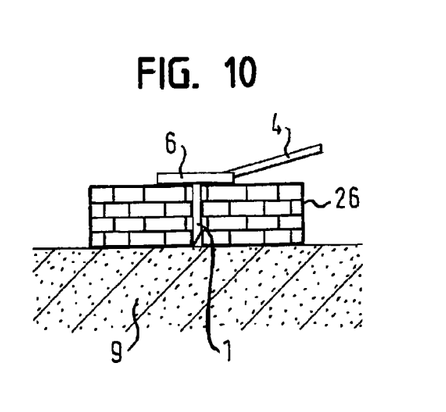
FIG. 10 shows another illustrative embodiment of the present invention.

FIG. 10 shows another illustrative embodiment of a cannula assembly in accordance with the present invention. The cannula assembly again consists of the injection cannula 1 with the pressure force distributor 6 and a cannula guide 26. The injection cannula 1 and the pressure force distributor 6 are formed as in the other illustrative embodiments. Like the cannula guide 10 of the first illustrative embodiment and in principle also the cannula guide 17 of the second illustrative embodiment, the cannula guide 26 is designed as a hollow chamber structure. However, the hollow chamber structure 26 of FIG. 10 is divided into a large number of hollow cells or hollow chambers. The hollow chamber structure 25 is anisotropic in the sense that it offers less resistance to deformation in the longitudinal direction of the penetrating portion 3 than it does to a deformation in the transverse direction.

In one embodiment, the hollow chamber structure 26 is a honeycomb structure with walls which between them enclose the cavities of the honeycomb structure and are arranged uniformly. The injection cannula extends through the honeycomb structure and is laterally supported and axially guided by the walls of the honeycomb structure.

Figure 11:
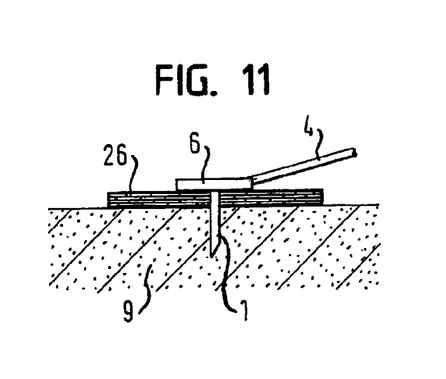
FIG. 11 shows the cannula assembly of FIG. 10 after insertion of the injection cannula into the skin.

FIG. 11 shows the cannula assembly of the embodiment of FIG. 10 with the injection cannula 1 inserted into the body tissue 9. The hollow chamber structure 26 has collapsed axially. The hollow chamber structure 26 is also provided on its underside with an adhesive surface for securing it on the body tissue 9.

Figure 12:
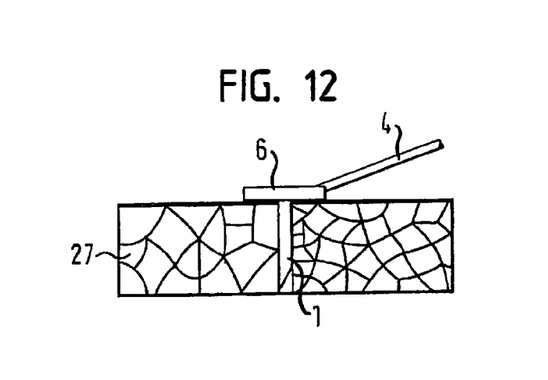
FIG. 12 shows another embodiment of the present invention.

FIG. 12 shows another illustrative embodiment of a cannula assembly, which is a modification of the embodiment of FIG. 10. A porous material forms the cannula guide 27 as a porous structure, which is likewise to be designated as a hollow chamber structure. The porosity of the material is a closed porosity, for example of the kind that sponge structures have. In FIG. 12, the hollow chamber structure 27 is shown with a coarser porosity on one side of the injection cannula 1 than on the other. However, actual cannula assemblies do not have this kind of difference in porosity, and instead they have a porosity comprising pores of randomly distributed pore size, although this porosity is uniformly present in the hollow chamber 27 seen as a whole.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection needle assembly comprising an injection needle which can be inserted into body tissue and a needle guide which can be positioned on the body tissue and stabilizes the injection needle against bending and buckling during an axial movement of the needle, wherein the needle guide comprises a hollow chamber structure which is axially compressible and surrounds and supports the injection needle, wherein the hollow chamber structure is a gas-filled balloon or comprises such a balloon, and wherein a support structure in the balloon supports the injection needle transverse to the needle's length.

2. The injection needle assembly as claimed in claim 1, wherein the needle guide is axially deformable into a state of minimal axial thickness.

3. The injection needle assembly as claimed in claim 2, wherein the needle guide is axially deformable elastically before reaching the state of minimal axial thickness.

4. The injection needle assembly as claimed in claim 2, wherein the needle guide comprises inner surfaces which adhere to one another in an axially compressed state of the needle guide.

5. The injection needle assembly as claimed in claim 1, wherein the needle guide is permanently axially deformable.

6. The injection needle assembly as claimed in claim 1, wherein the needle guides is axially compressible by the insertion of the injection needle into the body tissue.

7. The injection needle assembly as claimed in claim 1, wherein the needle guide can be axially deformed into a state in which it forms a plaster by which the injection needle can be fixed at the injection site in the inserted state.

8. The injection needle assembly as claimed in claim 7, wherein the needle guide comprises an adhesive surface, facing the body tissue during use, for fixing 30 the injection needle assembly at an injection site on the body tissue.

9. The injection needle assembly as claimed in claim 1, wherein the needle guide has an underside which can be positioned on the body tissue, a top face, and, between the underside and the top face, a flexible axial portion which can be deformed by a force exerted on the top face in the direction of the underside.

10. The injection needle assembly as claimed in claim 9, wherein on the top face there is a force distributor via which a force required for inserting the injection needle into the skin is transmitted to the needle guide.

11. The injection needle assembly as claimed in claim 10, wherein the force distributor is secured on the top face.

* * * * *